(12) United States Patent
Guenst et al.

(10) Patent No.: US 7,146,225 B2
(45) Date of Patent: Dec. 5, 2006

(54) METHODS AND APPARATUS FOR ACCESSING AND STABILIZING AN AREA OF THE HEART

(75) Inventors: Gary W. Guenst, Collegeville, PA (US); Gerard C. Forest, Whispering Pines, NC (US)

(73) Assignee: Medtronic, Inc., Minneapolis, MN (US)

( * ) Notice: Subject to any disclaimer, the term of this patent is extended or adjusted under 35 U.S.C. 154(b) by 515 days.

(21) Appl. No.: 10/283,794

(22) Filed: Oct. 30, 2002

(65) Prior Publication Data

US 2004/0088035 A1    May 6, 2004

(51) Int. Cl.
 *A61B 1/00* (2006.01)
(52) U.S. Cl. .................. 607/119; 607/127; 607/116
(58) Field of Classification Search ............. 607/119, 607/122, 126–132; 600/374, 386–7
See application file for complete search history.

(56) References Cited

U.S. PATENT DOCUMENTS

| 3,737,579 A | 6/1973 | Bolduc ................. 128/418 |
|---|---|---|
| 4,010,758 A | 3/1977 | Rockland et al. ........ 128/418 |
| 4,313,448 A | 2/1982 | Stokes ................. 128/785 |
| 4,357,946 A | 11/1982 | Dutcher et al. ........ 128/785 |
| 4,991,578 A | 2/1991 | Cohen ................. 128/419 |
| 5,139,033 A | 8/1992 | Everett et al. |
| 5,246,014 A * | 9/1993 | Williams et al. ........ 607/122 |
| 5,336,252 A | 8/1994 | Cohen ................. 607/119 |
| 5,464,447 A | 11/1995 | Fogarty et al. ......... 607/129 |
| 5,484,445 A | 1/1996 | Knuth ................. 606/129 |
| 5,522,875 A | 6/1996 | Gates et al. ........... 607/127 |
| 5,553,612 A | 9/1996 | Lundbäck .............. 128/643 |
| 5,575,814 A | 11/1996 | Giele et al. ........... 607/127 |
| 5,716,391 A | 2/1998 | Grandjean ............. 607/127 |
| 5,716,392 A | 2/1998 | Bourgeois et al. ...... 607/132 |
| 5,792,217 A | 8/1998 | Camps et al. .......... 607/119 |
| 5,827,216 A | 10/1998 | Igo et al. .............. 604/21 |
| 5,868,770 A | 2/1999 | Rygaard ............... 606/167 |
| 5,871,528 A | 2/1999 | Camps et al. .......... 607/119 |
| 5,871,532 A | 2/1999 | Schroeppel ............ 607/128 |
| 5,897,584 A | 4/1999 | Herman ............... 607/122 |

(Continued)

OTHER PUBLICATIONS

Cazeau, S., et al: "Four Chamber Pacing in Dilated Cardiomyopathy" PACE, vol. 17, Nov. 1994, Part II.

*Primary Examiner*—George Manuel
*Assistant Examiner*—Nicole R. Kramer
(74) *Attorney, Agent, or Firm*—Michael C. Soldner; Carol F Barry; Girma Wold-Michael

(57) ABSTRACT

An epicardial lead installation tool having an elongated tool body extending between a tool body proximal and distal ends and encloses a tool body lumen. At least one suction pad supported by a suction pad strut extends distally to a distal end surface of the tool body distal end. A lead implantation tool extending between implantation tool proximal and distal ends is inserted through the tool body lumen to dispose the implantation tool distal end proximate to the tool body distal end. The lead implantation tool distal end is adapted to engage the distal electrode head of an epicardial lead to enable the extension of the assembly of the of the lead installation tool, the lead implantation tool and the epicardial lead through a skin incision and to apply the suction pad against the epicardium. Suction is applied through the suction pad to affix it to the epicardium while the implantation tool proximal end is manipulated to affix the distal fixation mechanism to the myocardium at the implantation site.

31 Claims, 9 Drawing Sheets

U.S. PATENT DOCUMENTS

| | | | |
|---|---|---|---|
| 5,902,324 A | 5/1999 | Thompson et al. | 607/9 |
| 5,902,331 A | 5/1999 | Bonner et al. | 607/122 |
| 5,972,013 A | 10/1999 | Schmidt | 606/185 |
| 6,010,526 A | 1/2000 | Sandstrom et al. | 607/1 |
| 6,080,175 A | 6/2000 | Hogendijk | 606/185 |
| 6,132,456 A | 10/2000 | Sommer et al. | 607/127 |
| 6,185,464 B1 | 2/2001 | Bonner et al. | 607/119 |
| 6,193,652 B1 * | 2/2001 | Berky et al. | 600/205 |
| 6,219,579 B1 | 4/2001 | Bakels et al. | 607/17 |
| 6,231,518 B1 | 5/2001 | Grabek et al. | 600/508 |
| 2003/0212446 A1 * | 11/2003 | Kaplan et al. | 607/129 |

* cited by examiner

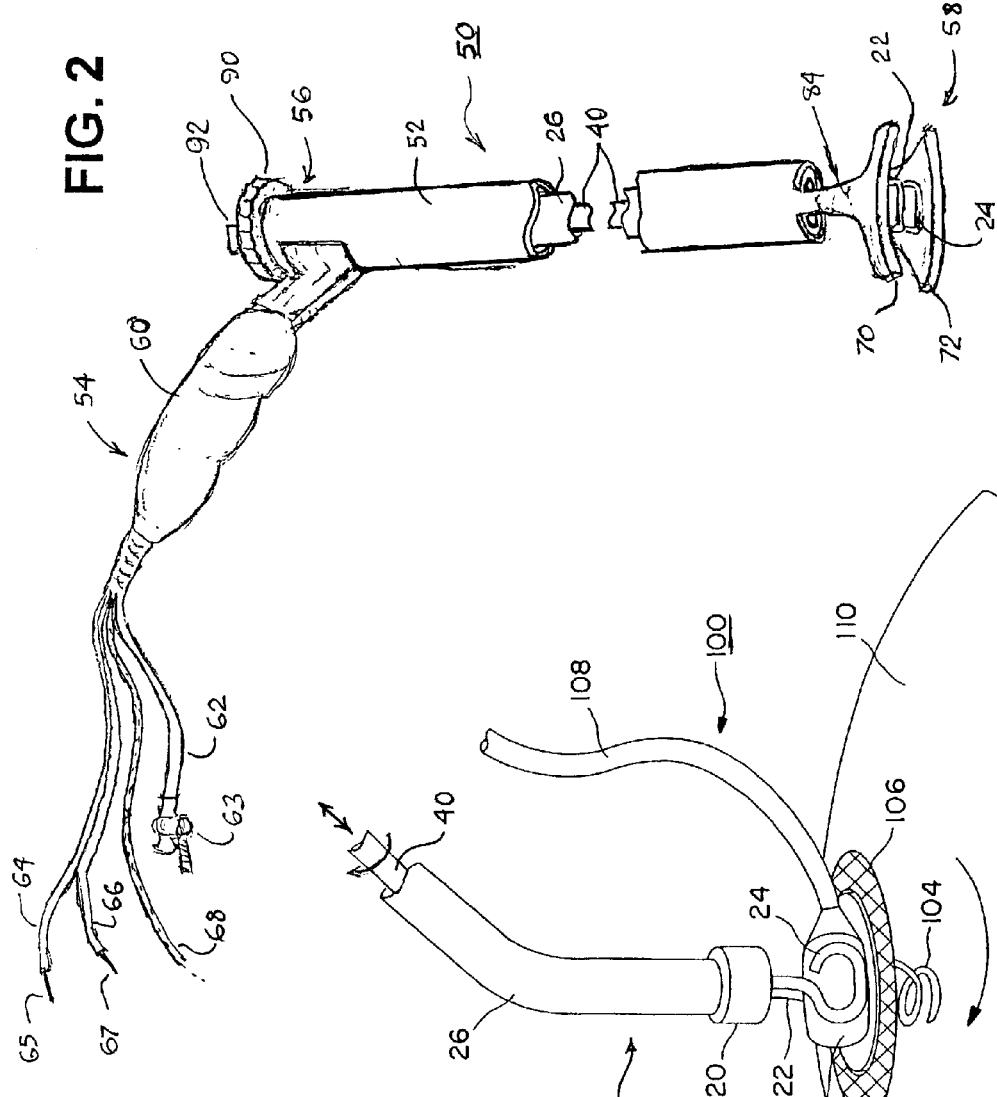

METHODS AND APPARATUS FOR ACCESSING AND STABILIZING AN AREA OF THE HEART

FIELD OF THE INVENTION

The present invention pertains methods and apparatus for accessing and stabilizing an area of the heart, particular a portion of the heart wall to enable performance of a surgical procedure through minimally invasive surgical techniques.

BACKGROUND OF THE INVENTION

Many minimally invasive surgical techniques and devices designed to reduce morbidity, expense, and the trauma associated with open-chest cardiac surgery have revolutionized cardiac surgery. Recent advances in endoscopic and thoracoscopic instruments and percutaneous access to a patient's thoracic cavity have made minimally invasive surgery possible. The advent of thoracoscopy in cardiac surgery has shown promise as a technique to enable surgeons to implant epicardial leads without sternotomy or thoracotomy. Thoracoscopy normally involves making small incisions between the ribs into the chest cavity and passing tubular ports Through the incisions. Illumination devices, cutting instruments, sutures, etc. may be inserted into the chest cavity via the ports. Approaches to accessing other sites of the left heart through the use of trocars and the racoscopes and various tools are described in U.S. Pat. Nos. 5,871,532 and 5,464,447, for example.

Other methods and apparatus that are introduced through percutaneously placed ports or directly through small transthoracic incisions for accessing the pericardial space employ suction devices to grip the pericardium or epicardium as disclosed, for example, in U.S. Pat. Nos. 4,991,578, 5,336, 252, 5,827,216, 5,868,770, 5,972,013, 6,080,175, and 6,231, 518. The suction devices are typically configured like a catheter or tube having a single suction lumen and typically having a further instrument delivery lumen. The suction lumen terminates in a single suction lumen end opening through the device distal end in the '578, '252, '175, '770, and '013 patents and through the device sidewall in the '216 and '518 patents. Certain of these patents recite that the applied suction draws a "bleb," i.e., a locally expanded region of the pericardium, into the suction lumen or a suction chamber at the device distal end. A needle can then be advanced into the bleb and used to draw off fluids or deliver drugs into the pericardial space, or the like. In addition, it is suggested in these patents that treatment devices including catheters, guidewires, and electrodes, e.g., defibrillation electrodes, can be advanced into the pericardial space through a device introduction lumen for a variety of reasons. Although theoretically plausible, the ability to reliably maintain a vacuum seal against the pericardium when such treatment devices are advanced can be problematic.

One particular proposed use of such devices and procedures is to implant cardiac pacing and/or cardioversion/defibrillation leads, particularly to attach the electrodes of such leads to or within the heart wall.

In the field of cardiac stimulation, cardiac pacing leads having bipolar and unipolar pace/sense electrodes have long been used in conjunction with implantable pulse generators (IPGs) to conduct pacing pulses or cardioversion/defibrillation shocks generated by the IPG to a site of the heart and cardiac signals from the site to the IPG. Cardioversion/defibrillation leads and pacing leads are typically provided with a passive fixation or an active fixation mechanism at the lead body distal end that is passively or actively engaged with cardiac tissue to anchor a distal tip electrode at a desired site in or on the heart. Passive fixation generally involves an atraumatic fixation lodging the distal electrode against the endocardium or within a coronary blood vessel. Positive or active fixation generally involves a more traumatic penetration of a fixation mechanism into the myocardium from an endocardial or epicardial surface, and the active fixation mechanism commonly comprises a distal electrode.

Endocardial pacing and cardioversion/defibrillation leads having either active fixation or passive fixation mechanisms are implanted by a transvenous route into a heart chamber to locate the distal electrode(s) at a selected site in the heart chamber where an active or passive fixation mechanism is deployed to maintain the electrode affixed at the site. Epicardial leads are implanted by exposure of the epicardium of the heart typically through a limited subxiphoid approach or a more extensive surgical exposure made to perform other corrective procedures. The distal end of the epicardial lead formed with one or two electrodes and an active fixation mechanism supported by an electrode head is affixed to the epicardium. Typically, the active fixation mechanism comprises the single electrode or one of the bipolar electrodes, but can be separate and electrically isolated from the electrodes.

Epicardial pacing and cardioversion/defibrillation leads were the first to be implanted widely, because endocardial leads lacked effective active or passive fixation mechanisms and relied upon relatively stiff lead bodies that cause perforations and dislodgement of the distal electrode(s) or fracture of the lead conductor. Initially, access to the epicardium was made by a thoracotomy or median sternotomy and excision through or removal of the pericardial sac. Typically, pace/sense electrodes penetrated the myocardium and were sutured against the epicardium to maintain fixation. The large surface area patch electrodes of cardioversion/defibrillation electrodes were sutured to the epicardium.

Improvements were made in epicardial pace/sense leads to reduce the surgical trauma involved in accessing the epicardium and to avoid the need to suture the electrode to the epicardium through the use of active fixation mechanisms. Such active fixation mechanisms of epicardial pacing leads typically comprise a tissue penetrating, self-affixing mechanism extending away from a support or base or plate of the electrode head. The fixation mechanism is forced into the myocardium typically employing an introduction tool engaging the electrode head until it is fully seated within the endocardium and the plate bears against the epicardium. The plate is typically formed with a tissue ingrowth encouraging fabric or lattice, whereby tissue ingrowth about the plate assists in chronic anchoring to the heart. Such active fixation mechanisms typically comprise either or both of a helix or hook having a sharpened tip that is coupled with a lead conductor within the electrode head.

An active fixation, unipolar, epicardial lead having a barbed hook is disclosed in commonly assigned U.S. Pat. No. 4,313,448 and embodied in the MEDTRONIC® Model 6951 lead. The active fixation mechanism comprises forward facing barbed electrode having the tip at a predetermined angle with relation to the shank of the electrode and with respect to a flexible base pad or plate of the electrode head. The plate has a substantially centered hole and a plurality of outer holes for fibrous ingrowth, and the shank of the electrode extends out through the substantially centered hole. The barbed electrode is pushed into the myocardial tissue to the point where the base pad engages against the epicardium thereby indicating full implantation within the myocardium. During implantation, a stiffening stylet is employed to stiffen the lead body and a forceps is employed to grasp the electrode head to push the barb into the myocardium.

The MEDTRONIC® Model 6917 epicardial pacing lead and subsequently introduced epicardial pacing lead models support the helix to extend at 90° to the plate as disclosed in commonly assigned U.S. Pat. Nos. 3,737,579 and 4,010,758. Other variations of such epicardial screw-in leads include multiple co-axial and intertwined helixes or a helix axially surrounding a pin extending coaxially with the helix axis from the electrode head. During implantation, the lead body and electrode head are mounted to an elongated implantation tool, and the sharpened tip of the helix is advanced through the incision to perforate the epicardium. The tool and lead are rotated to screw the helix into the myocardium until the plate abuts the epicardium, and the electrode head is detached from the tool. Alternatively, the sides of the electrode head are grasped by tongs and that are rotated to screw the helix into the myocardium until the plate abuts the epicardium, and the electrode head is detached from the tongs as disclosed in commonly assigned U.S. Pat. No. 6,010,526.

A further epicardial screw-in lead is disclosed in commonly assigned U.S. Pat. No. 4,357,946 wherein the helix is mounted to a gear mechanism within the electrode head. The helix can itself be rotated to screw into the myocardium without rotating or moving the electrode head by a rotation of a removable stylet extending through the length of the lead body and engaging the gear mechanism. Both unipolar and bipolar embodiments are disclosed.

The implantation of such epicardial leads is usually through general thoracic surgery; either via a median sternotomy or intercostal approach or via a more limited subxiphoid approach. These procedures involve major surgery that may be painful and dangerous for the patient and can be costly. The subxiphoid approach, moreover, only permits limited access to the anterolateral surface of the left ventricle and does not provide any access at other locations of the left ventricle or the left atrium.

By contrast, the percutaneous implantation of endocardial leads became much less traumatic, faster, and less costly, and the deficiencies of early endocardial pacing leads were overcome. Over the years, endocardial pacing leads were improved by incorporation of effective and easy to use active and passive fixation mechanisms to overcome the problems of dislodgement. Moreover, lead bodies were made stronger, more flexible, smaller in diameter, and more reliable. Fixation of pace/sense electrodes in the right atrium, right ventricle and within the coronary sinus and great vein descending from the coronary sinus became possible. Endocardial cardioversion/defibrillation leads were also developed incorporating these improved features of pacing leads and elongated cardioversion/defibrillation electrodes for implantation in the same locations.

Because of these improvements, endocardial pacing and cardioversion/defibrillation leads largely supplanted epicardial pacing and cardioversion/defibrillation leads in clinical practice. Epicardial pacing leads remained medically indicated for some patients, particularly children, or patients undergoing oven heart surgery for other reasons. Although the various indications for epicardial lead fixation in pediatric patients are numerous, some common factors include small stature, congenital heart defects with residual or potential right to left shunting or single ventricle hearts, or lack of venous access to the chamber requiring pacing.

The left ventricle has a greater wall thickness (10–20 mm as compared to 1–5 mm) than the right ventricle because the left ventricle of the heart must pump oxygenated blood throughout the body while the right ventricle only pumps venous blood through the lungs to be oxygenated. Because the left heart is relatively more important for hemodynamic output, not surprisingly, various pathologies may be better treated through pacing of the left heart. For example, in patients with dilated cardiomyopathy and congestive heart failure, electrical stimulation of both the right and left heart chambers has been shown to be of major importance to improve the patient's well being and manage heart failure. See, for example, Cazeau et al., "Four Chamber Pacing in Dilated Cardiomyopathy," *PACE*, November 1994, pgs. 1974–79. See also the pacing systems providing synchronized right and left heart chamber pacing of heart failure patients disclosed in U.S. Pat. Nos. 5,716,392, 5,902,324, and 6,219,579. Recently, several right and left heart pacemakers and implantable cardioverter-defibrillators incorporating right and left heart pacing functions have been approved for clinical implantation in patients suffering from congestive heart failure.

Endocardial pacing electrodes cannot be implanted directly within the left heart chambers due to risk of thrombus formation about the lead body and electrode surfaces. Blood flows through the right heart chambers (atrium and ventricle), through the lungs, through the left heart chambers (atrium and ventricle) and then through the rest of the body, including the brain, before returning again to the right atrium. Implanted objects often cause minor blood clots and thrombus to form in the blood. These may, on occasion, dislodge and be released into the bloodstream. Any blood clots or thrombi, however minor, that form in the left atrium and ventricle could have serious consequences if they were to break free and be swept into the brain and cause a stroke. In contrast, clots or thrombi released from an object implanted in the right side of the heart would simply travel to the lungs, where they would lodge, usually without serious risk.

Consequently, endocardial leads are directed through the coronary sinus to locate pace/sense or cardioversion/defibrillation electrodes in the coronary sinus or great vein in order to pace and sense and/or cardiovert/defibrillate the left heart. The possible sites for lodging the pacing and/or cardioversion/defibrillation electrodes relative to the left atrium or left ventricle are necessarily limited by the coronary sinus and great vein. At times it is difficult to advance the pacing and/or cardioversion/defibrillation electrodes into or to a desired site of the coronary sinus or great vein. And, the lead bodies tend to fibrose into the coronary sinus or great vein over time and become difficult or impossible to remove if it becomes desirable to do so.

Therefore, interest in implanting epicardial pacing and cardioversion/defibrillation electrodes at a variety of left heart sites to provide the most efficacious left and right heart pacing for the patient suffering from congestive heart failure has increased in recent years.

Despite these improvements a need exists for a simple way to attach a pace/sense electrode of a pacing lead to the epicardium or to perform various other procedures through a small diameter transthoracic port or incision.

SUMMARY OF THE INVENTION

The present invention is preferably embodied in an epicardial suction tool for engaging the epicardium having an elongated tool body extending between a tool body proximal and distal ends and encloses a tool body lumen. At least one suction pad supported by a suction pad strut extends distally to a distal end surface of the tool body distal end. Suction is applied through suction lumens to suction ports of the suction pad that fix to the epicardium so that the suction tool distal end tracks movement of the epicardium. Various procedures can be performed and medical devices, instruments, drugs can be advanced through the tool body lumen without interrupting suction.

In one embodiment of the present invention, a lead implantation tool extending between implantation tool proximal and distal ends is inserted through the tool body lumen to deploy the implantation tool distal end proximate to the tool body distal end. The lead implantation tool distal end is adapted to engage the distal electrode head of an epicardial lead to enable the extension of the assembly of the lead installation tool, the lead implantation tool and the epicardial lead through a skin incision and to apply the suction pad against the epicardium. Suction is applied Through the suction pad to affix it to the epicardium while the implantation tool proximal end is manipulated to affix the distal fixation mechanism to the myocardium at the implantation site.

In one embodiment, the epicardial suction tool and lead implantation tool are combined into a single tool.

In a variation of the epicardial suction tool and lead implantation tool embodiments, one or more pace/sense threshold measurement electrode is incorporated into the suction pad or pads so that pacing and sensing threshold measurements can be made prior to affixing the distal fixation mechanism to the myocardium at the implantation site.

The epicardial suction tool can comprise a light source for illuminating the site of the epicardium that the suction pad or pads are affixed to.

A handle is preferably incorporated into the epicardial tool extending laterally to the tool body proximal end for convenience of manipulating the epicardial suction tool.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 1 is a partial perspective view of the fixation of the helical electrode of an exemplary epicardial screw-in lead to the myocardium employing retractable tongs to hold the electrode head during fixation;

FIG. 2 is a perspective view of a preferred epicardial lead installation tool of the present invention;

DETAILED DESCRIPTION OF THE PREFERRED EMBODIMENTS

Figure 3:
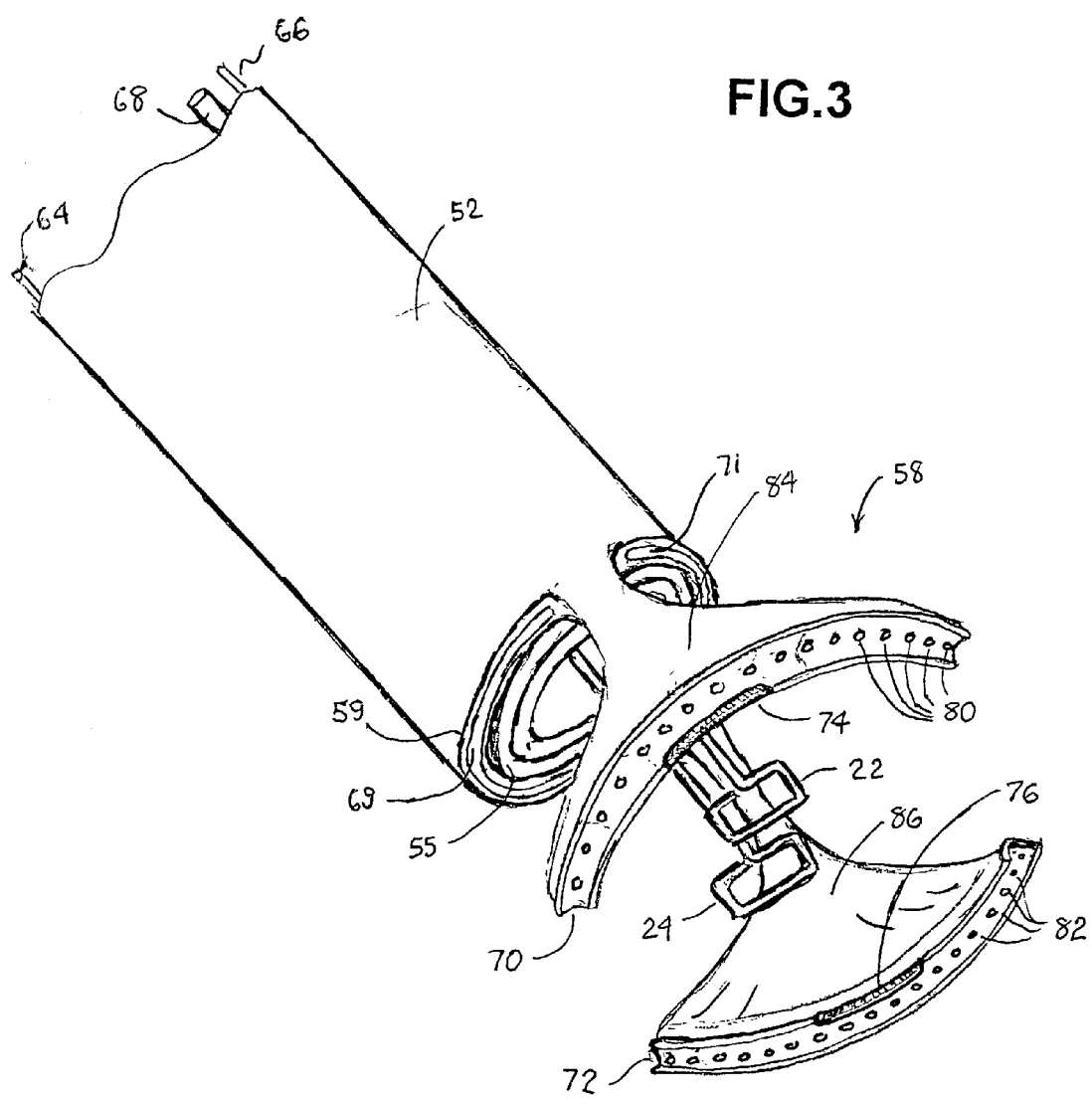
FIG. 3 is an expanded partial perspective view of the distal segment of the lead installation tool of FIG. 2.
Figure 4:
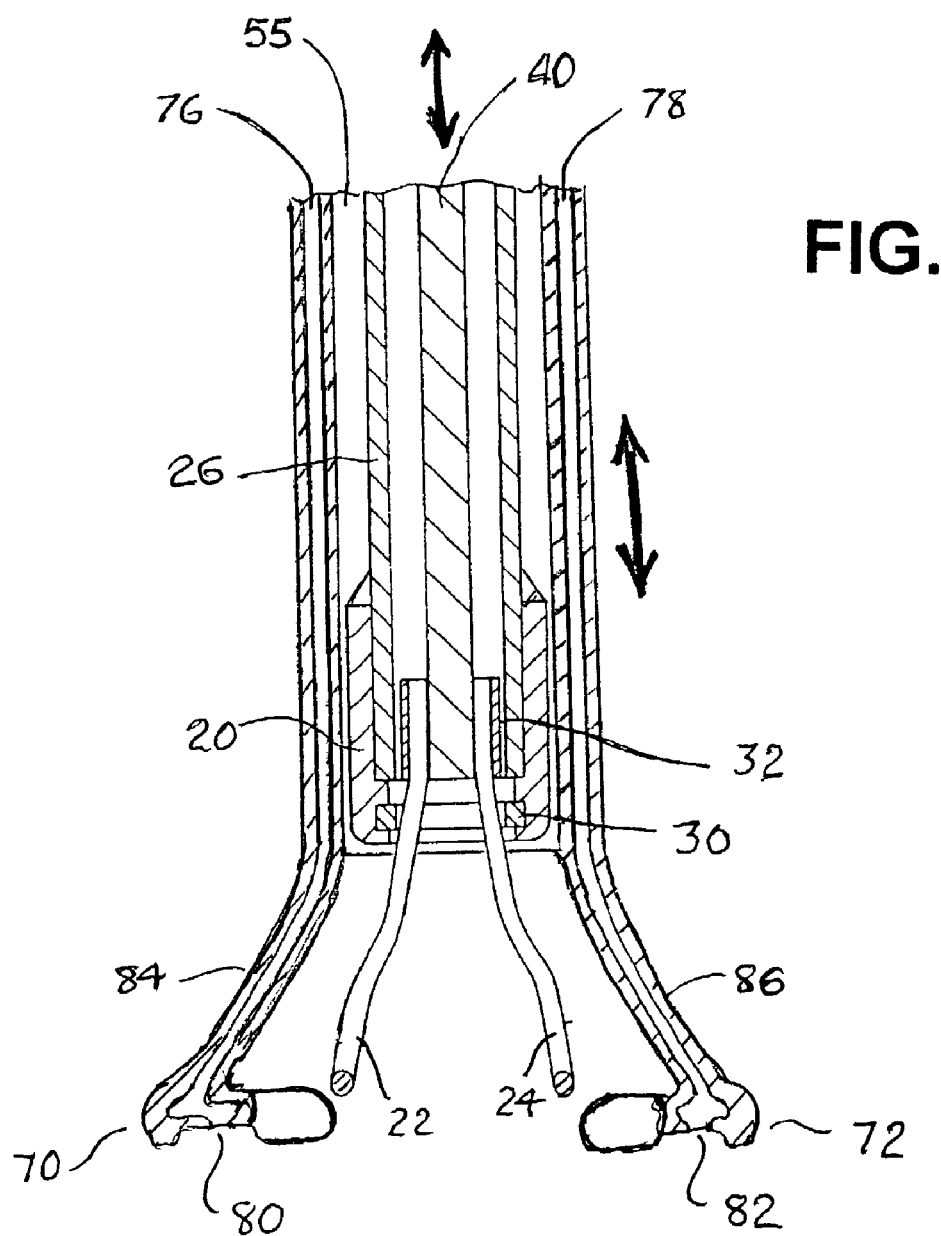
FIG. 4 is a cross-section view of the distal segment of the lead installation tool of FIG. 2.

In the following detailed description, references are made to illustrative embodiments for carrying out the invention. It is understood that other embodiments may be utilized without departing from the scope of the invention.

FIG. 1 is a plan view of an implantation tool 10 of the type disclosed in the above-referenced '526 patent, which is incorporated into a preferred embodiment of the epicardial lead installation tool of the present invention, gripping the electrode head 102 of an epicardial screw-in lead 100 to screw the helical electrode 104 through the epicardium accessed through a surgical incision into the myocardium 110. The implantation tool 10 comprises outer shaft tubing 26 having a lumen extending between the device proximal end (not shown) and the distal nose cap 20. An internal shaft or cable 40 extends through the lumen of the outer shaft tubing 26 between a pair of spaced apart tongs 22 and 24 and a proximal handle assembly (not shown) that enables selective rotation as well as distal and proximal movement of the cable 40 and tongs 22 and 24.

The tongs 22 and 24 are affixed to the cable distal end by a crimp 30 and extend through a circular bearing encased in the distal nose 20. As described in the '526 patent, the cable proximal end is spring-loaded so as to normally urge the cable 40 proximally, which brings the tongs 22 and 24 together toward one another. The handle assembly includes a movable portion that can be manipulated against the spring force to extend the cable 40 and tongs 22 and 24 distally away from the distal nose 20 whereupon the tongs 22 and 24 spread apart. The tongs 22 and 24 are spring biased outward from nose cap 20 so that they slide against bearing 30 and extend distally and spread apart as tension on the cable 40 is released so that the electrode head 102 may be inserted between or released from the tongs 22 and 24.

The depicted epicardial pacing lead 100 can take any of the known forms that have a fixation helix 104 extending from an electrode head 102 adapted to be rotated and screwed into the myocardium 110. The fixation helix 104 typically is electrically connected to a lead conductor within elongated lead body 108 so that the fixation helix can function as a pacing and/or sense electrode. The depicted fixation helix 104 extends away from the distal end surface of electrode head 102 at right angles to the lead body 108 that is joined to the electrode head 102 in the manner of the above described Model 6917 and subsequent model epicardial pacing leads disclosed in commonly assigned U.S. Pat. No. 3,737,579. A DACRON® fiber mesh skirt 106 extends outward from the distal surface of the electrode head 102 that body tissue grows into over a period of chronic implantation.

In use, the handle assembly is manipulated so that the tongs 22 and 24 are extended distally from distal nose 20 and spread apart, the electrode head 102 is positioned between the spread apart tongs 22 and 24, and the handle assembly is released so that the tongs 22 and 24 retract proximally to bear against and grip the opposite sides of the electrode head 102. The distal tip of the fixation helix 104 is applied against the epicardium, and the rotatable portion of the handle assembly is rotated clockwise while the outer shaft tubing 26 remains stationary. The handle rotation is transferred through the inner cable 40 to the tongs 22 and 24 to screw the fixation helix 104 into the myocardium 110.

A preferred embodiment of an epicardial lead installation tool 50 of the present invention incorporating certain of these features of the implantation tool 10 is depicted in FIGS. 2–8. However, in the preferred embodiment of the present invention, the rotation of the electrode head 102 and fixation helix 104 is effected by simultaneously rotating both the outer shaft tubing 26 and the inner cable 40 in the same direction. The inner cable 40 is moved proximally and distally with respect to the outer shaft tubing 26 to move the tongs 22 and 24 together and apart, respectively, to grip and release, respectively, the sides of the electrode head 102.

The epicardial lead installation tool 50 incorporates a capability of applying suction to the epicardium to track movement of or stabilize the myocardium 110 while the fixation helix 104 is screwed into the myocardium 110. The epicardial lead installation tool 50 optionally incorporates the capability of measuring sensing and pacing thresholds of the myocardium adjacent to the fixation site before the fixation helix 104 is screwed into the myocardium 110. The epicardial lead installation tool 50 further optionally includes the capability of illuminating the implantation site.

Figure 5:
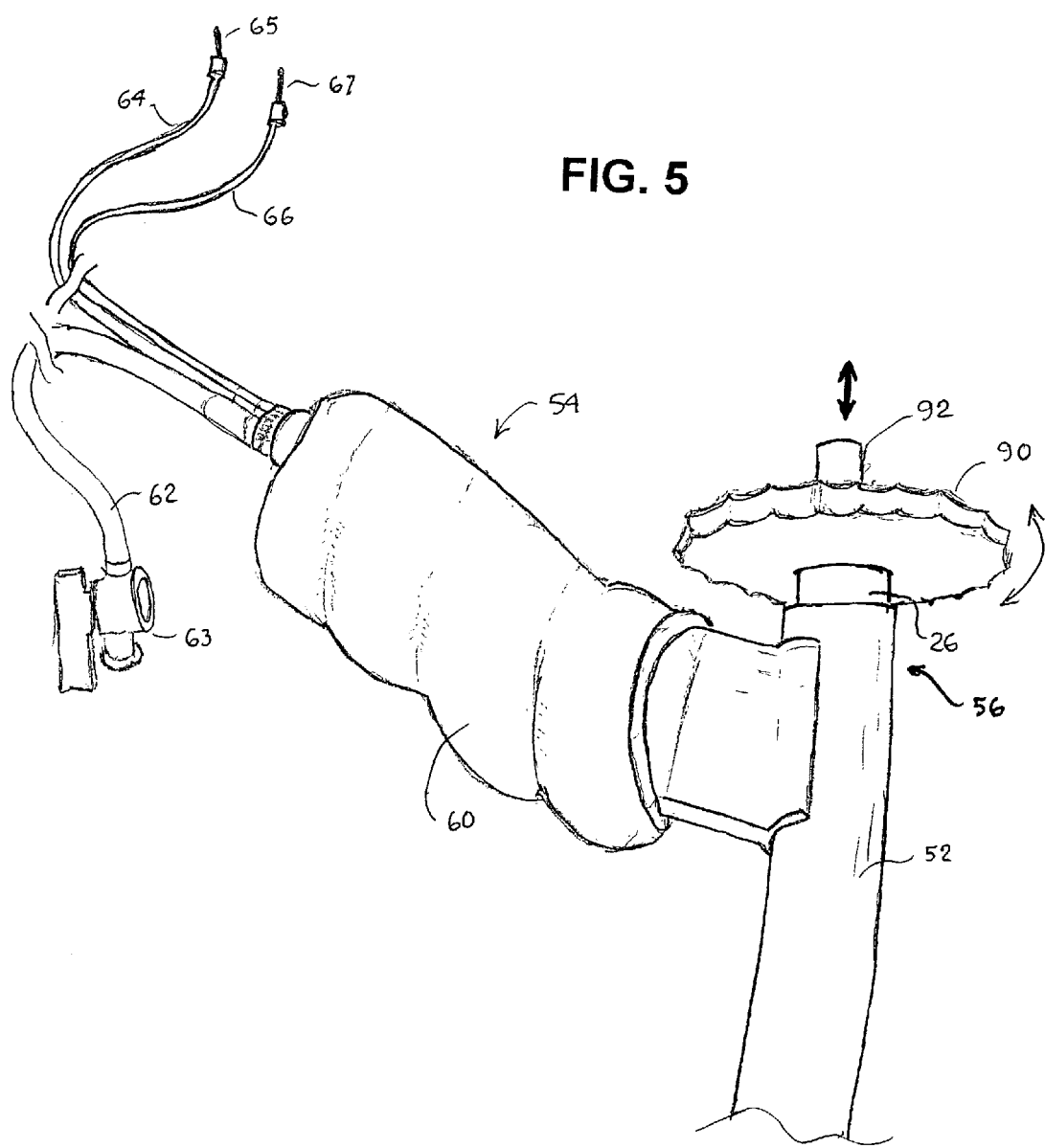
FIG. 5 is an expanded partial perspective view of the proximal segment of the lead installation tool of FIG. 2.

The epicardial lead installation tool 50 comprises an elongated tool body 52 and a tool handle 54 extending laterally from the tool body proximal end 56 shown in greater detail in FIG. 5. The tool handle 54 is shaped to provide a handgrip 60 that can be grasped by the user to position the tool body distal end 58, shown in greater detail in FIGS. 3 and 4, at the desired site of attachment.

The elongated tool body 52 is generally cylindrical, and a tool body lumen 55 extends between lumen end openings at the tool body proximal end 56 and tool body distal end surface 59 at tool body distal end 58. The portions of the implantation tool 10 depicted in FIG. 1, including the coaxially disposed outer shaft tubing 26 and cable 40, extend through the tool body lumen 55. The tongs 22 and 24 and distal nose 20 are disposed adjacent to or extending from the distal lumen end opening as shown in detail in FIGS. 3 and 4.

At the tool body proximal end 56, the proximal end of the outer shaft tubing 26 is coupled to a thumbwheel 90, and the proximal end of the cable 40 is selectively engaged by the push-button 92 to push cable 40 distally. The push-button 92 is spring-loaded to normally tension the cable 40 and draw the tongs 22 and 24 proximally and together as long as the push-button 92 is not depressed. The user can grip the handgrip 60 and selectively rotate the thumbwheel 90 to rotate the outer shaft tubing 26, cable 40 and tongs 22 and 24 or depress the pushbutton 92 to move the tongs 22 and 24 distally and apart from one another to release the electrode head 102.

The rotation of the thumbwheel 90 can be governed to both rotate and distally (or proximally) advance the outer shaft tubing 26, cable 40, axially and longitudinally within lumen 55. Coarse mating threads in the manner of a screw jack are formed between the outer surface of the outer shaft tubing 26 and the inner surface of the tool body 52 at the tool body proximal end 56. Thus, rotation of the thumbwheel 90 a set number of turns from the retracted position depicted in FIG. 6 rotates tongs 22 and 24 and advances tongs 22 and 34 a set distance axially to an advanced position depicted in FIG. 7.

Figure 6:
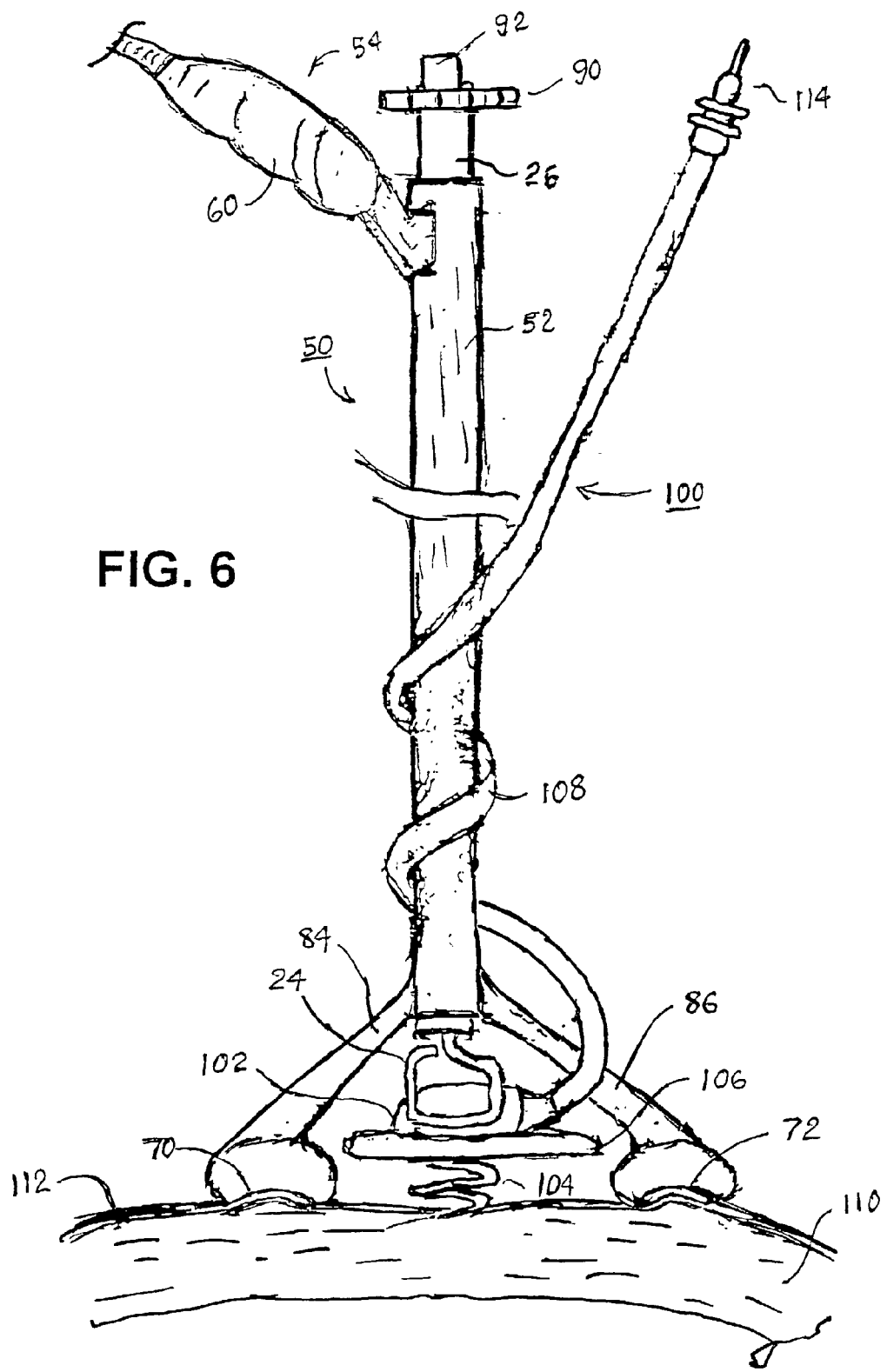
FIG. 6 is a perspective view of an epicardial screw-in lead assembled with the installation tool of FIG. 2 poised to enable rotation of the helical electrode into the epicardium.

The assembly of the outer shaft tubing 26, cable 40, and the thumbwheel 90 and push-button 92 are therefore preferably movable longitudinally within the tool body lumen 55 so that the relative distal positioning of the suction pads 70, 72 with respect to the electrode head 102 can be optimized so that the suction pads 70 and 72 can be placed in contact with and grasp the epicardium before the fixation helix 104 penetrates the epicardium as shown in FIG. 6.

The tool handle 54 encloses a suction lumen (not shown) that extends between a flexible vacuum line 62 terminating in a stopcock 63 and suction lumens 76 and 78 within the elongated tool body 52 that extend to suction ports 80 and 82 arrayed along the distal suction pads 70 and 72, respectively. The suction lumens 76 and 78 extend within the wall of the elongated tool body through the suction pad struts 84 and 86 supporting the suction pads 70 and 72, respectively, and to each of the suction ports 80 and 82 within the concave distal surfaces of suction pads 70 and 72, respectively. It will be understood that suction lumens 76 and 78 can be combined into a single suction lumen through most of the length of the elongated tool body 52 and branching apart at the distal tool body end 58 and into the suction pad struts 84 and 86. It will also be understood that the suction lumens 76 and 78 can comprise a tube or tubes extending outside and alongside the elongated tool body 52 to a manifold extending around the tool body distal end 58 from which the suction pad struts 84 and 86 extend distally.

The suction pads 70 and 72 are preferably formed in an arcuate shape to extend through arcs of about 45° around the tongs 22 and 24. However, it will be understood that the suction pads 70 and 72 can be combined to extend through 360° or in a C-shape through about 270°. The distal surfaces of the suction pads 70 and 72 are also preferably concave to optimize gripping of the epicardium. The suction ports 80 and 82 are preferably evenly spaced apart along the concave distal surfaces of the suction pads 70 and 72. The suction pad struts 84 and 86 supporting the suction pads 70 and 72, respectively, are preferably flexible and capable of bending outward when they are loaded by applied force.

Preferably, depression of the pushbutton 92 also actuates a valve that closes the suction lumens 76 and 78 and halts or interrupts suction to thereby release the epicardium at the same time that the tongs 22 and 24 move distally and apart from one another to release the electrode head 102. Or, a suction release push-button or trigger can be incorporated into the tool handle 54. Or, the vacuum can be interrupted by closing stopcock 63.

Optionally, a pair of conductors 64' and 66' depicted in FIG. 3 extend between connector elements 65 and 67 of respective flexible lead bodies 64 and 66 and then through the tool handle 54 and the elongated tool body 52 to respective pace/sense threshold measurement electrodes 74 and 76 along the distal suction pads 70 and 72. The measurement electrodes 74 and 76 are drawn into intimate contact with the epicardium when suction is applied through the adjacent suction ports 80 and 82. The connector elements 65 and 67 are connected with a pacing system analyzer (PSA) or the pacemaker implantable pulse generator (IPG) to measure and assess the pacing energy sufficient to capture the heart and the amplitude of the cardiac signals of interest in a manner well known in the art. The conductors 64 and 66 can extend in lumens of the side wall of the tool body 52 or simply be supported within electrically insulating tubes extending along the outer surface of the tool body 52 from the junction of tool handle 54 with tool body 52, along the suction pad struts 84 and 86, respectively, and to the pace/sense threshold measurement electrodes 74 and 76, respectively.

Furthermore, the implantation site is optionally illuminated with light provided by a light source, e.g. a miniaturized lamp mounted at the at the tool body distal end 58 that can be powered through conductors extending proximally to the too body proximal end and handle 60. Or the light can be transmitted from an external light source through a light conductor 68 which can be a light pipe or fiber-optic cable extending through handle 54 and within or alongside elongated tool body 52 to a terminus at the tool body distal end 58 forming a light-emitting lens or window. For example, the light can be emitted about the implantation site by making the suction pad struts 84 and 86 and/or the suction pads 70 and 72 of a transparent plastic material that acts like a light pipe and the surfaces act as light-emitting windows. The light pipe or fiber optic cable light conductor 68 is terminated in the suction pad struts 84 and 86 and/or the suction pads 70 and 72 that are then illuminated and operate to distribute the light around the implantation site.

Alternatively, the light pipe or fiber optic cable light conductor 68 can terminate in arcuate, light-emitting windows 69 and 71 extending around the end surface 59 at tool body distal end 58 as shown in FIG. 3. The entire tool body 52 can be formed of a light transmitting plastic that is painted or coated with an opaque coating, thereby constituting the light conductor 68, except at the end surface 59, thereby providing the arcuate, light-emitting windows 69 and 71 between the suction pad struts 84 and 86. The suction pad struts 84 and 86 can be formed integrally with the tool body 52 or the same material and be selectively exposed from the opaque coating so that light is emitted from the exposed surfaces as light emitting windows. The light conductor 68 is schematically illustrated as connected with the tool body 52 in FIG. 3, and the connection can be made at the junction of the tool handle 54 with such a light conducting tool body 52 shown in FIG. 5.

Figure 7:
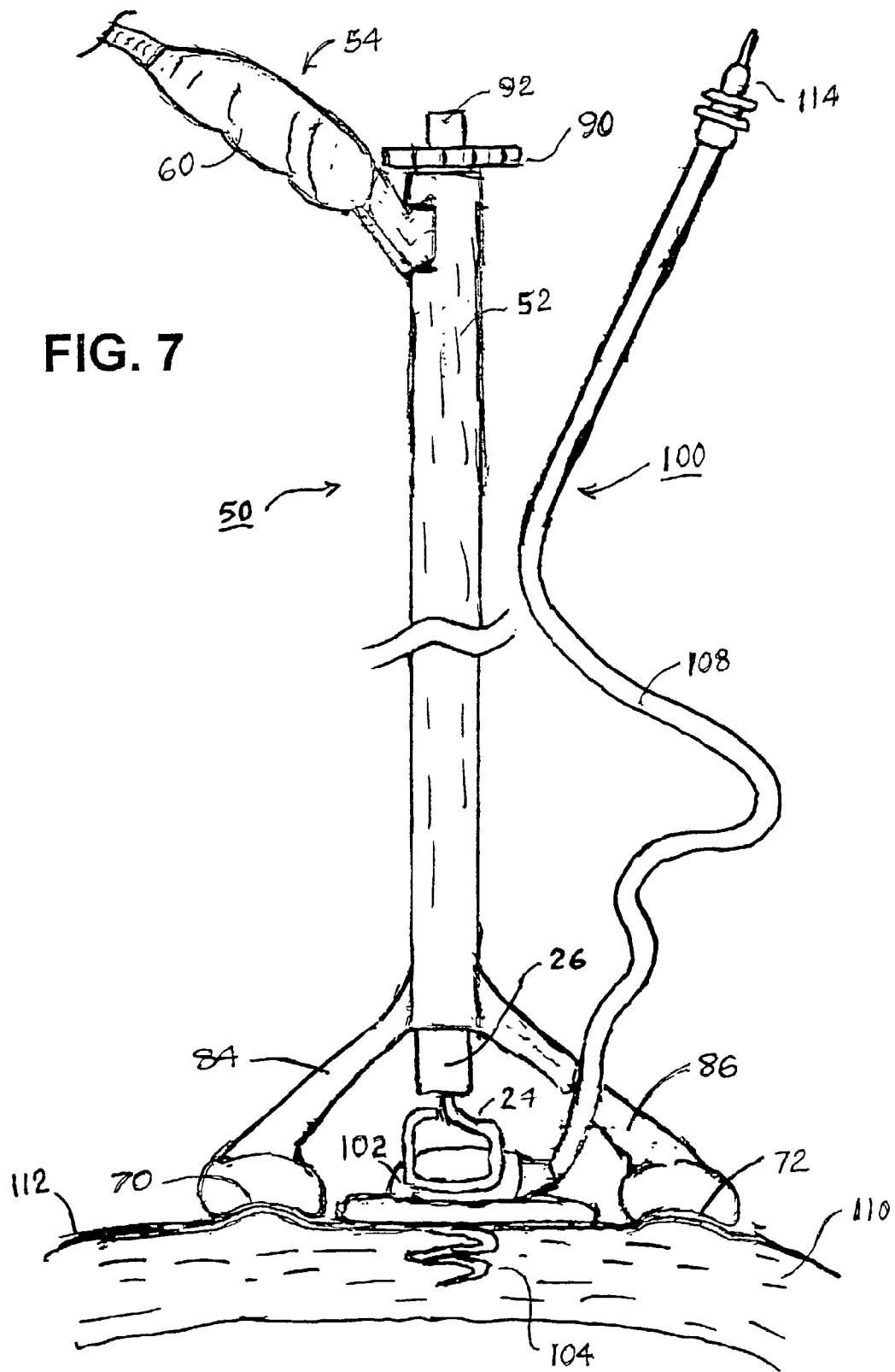
FIG. 7 is a perspective view of the epicardial screw-in lead assembled with the installation tool of FIG. 2 after rotation of the helical electrode into the epicardium.
Figure 8:
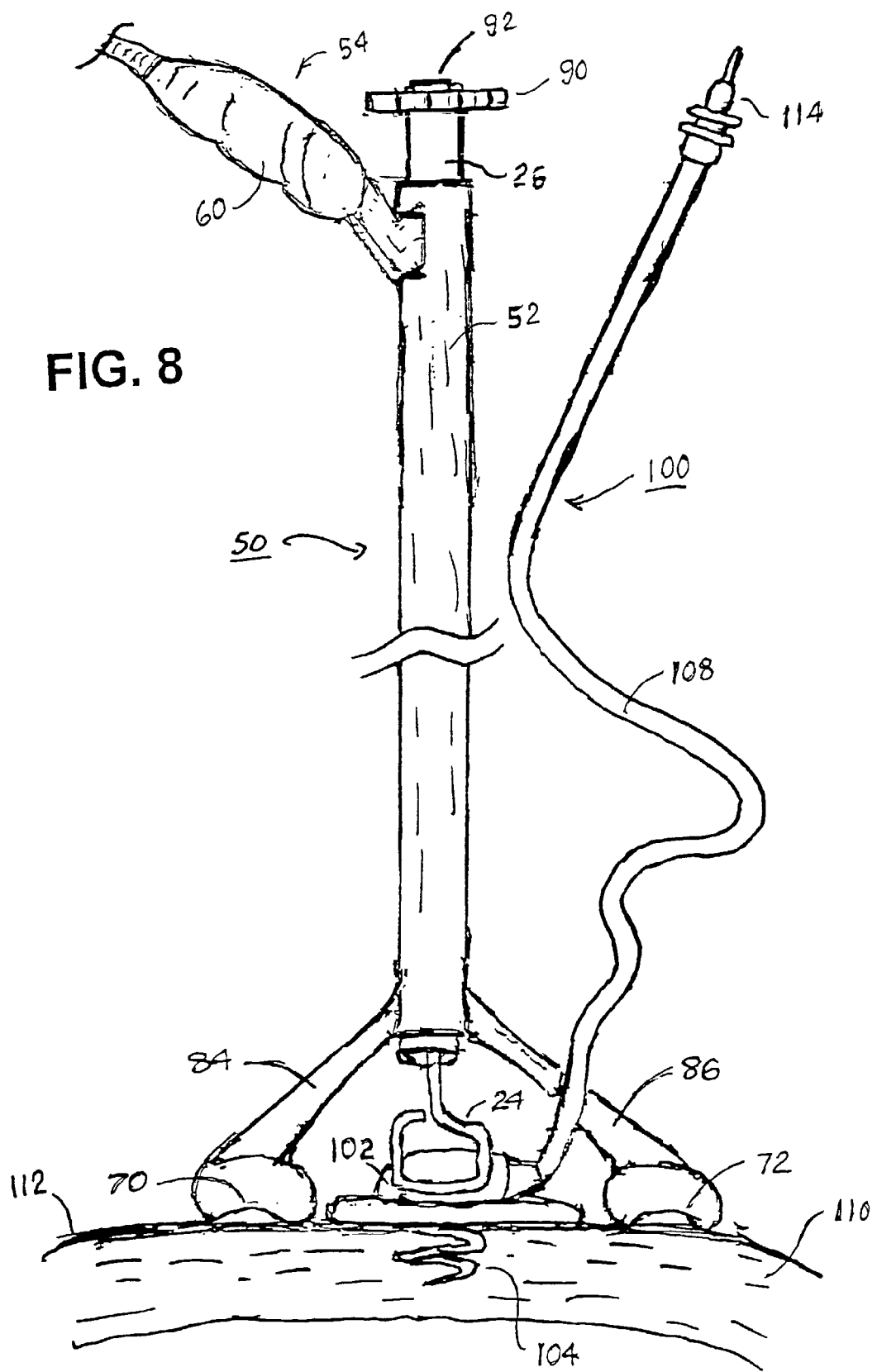
FIG. 8 is a perspective view of the epicardial screw-in lead being released from the installation tool of FIG. 2 after rotation of the helical electrode into the epicardium.

FIGS. 6–8 illustrate steps of implanting an epicardial screw-in lead 100 employing the epicardial lead installation tool 50. The assembly of the epicardial screw-in lead 100 and the epicardial lead installation tool 50 is depicted in FIG. 6 with suction applied through suction ports 80 and 82 to affix the suction pads 70 and 72 to the epicardium 112. The electrode head 102 is grasped by the tongs 22 and 24 in the manner described above prior to the application of suction. The tongs 22 and 24 and the electrode head 102 are retracted proximally as depicted in FIG. 6. The lead body 108 is wrapped around the elongated tool body 52 in a number of turns approximately equal to the number of turns required to screw the fixation helix 104 through the epicardium 112 and into the myocardium 110 as shown in FIG. 6.

Suction is then enabled through the suction pads 70 and 72 to the epicardium 112, and the lead installation tool 50 is thereby coupled to and tracks the movement of the heart. The applied suction may also stabilize the implantation site to some extent. Sensing and pacing threshold measurements can be performed through the electrodes 74 and 76, if incorporated into the surfaces of the suction pads 70 and 72, to make certain that the area of fixation of the lead electrode to the myocardium 110 is electrically active and does not comprise scar tissue due to injury or infarction. The site can be illuminated as described above through the fiber optic cable 68 (FIG. 2) to enable visualization of the fixation of the fixation helix 104 into the myocardium 110.

Then, the thumbwheel 90 is rotated to rotate and distally advance the outer shaft tubing 26, cable 40, within lumen 55, and tongs 22 and 24 a set number of turns and a set distance governed by the internal screw jack threads so that the sharpened tip of the fixation helix 104 penetrates the epicardium 112 and into the myocardium 110 as shown in FIG. 7. The lead body 108 is also unwound from the elongated tool body 52 as the fixation helix 104 is screwed into the myocardium. The lead connector 114 can be coupled to the pacemaker IPG or a PSA to double-check pacing and sensing thresholds. The thumbwheel 90 can be rotated in the opposite direction to unscrew the fixation helix 104 from the myocardium 110 if pacing and/or sensing thresholds are not satisfactory.

The release of the tongs 22 and 24 from the sides of the electrode head 102 and the release of suction of the epicardium 112 are illustrated in FIG. 8. The suction is interrupted either by a valve actuated when push-button 92 is depressed as shown or otherwise employing a trigger in tool handle 54 or simply closing stopcock 63. The tool handle 54 is drawn proximally with respect to the incision while the depression of the push-button 92 causes the tongs 22 and 24 to be advanced distally to spring outward and release electrode head 102. The epicardial lead installation tool 50 can then be withdrawn. The lead body 108 is subcutaneously routed to the site of implantation of the pacemaker IPG and attached to the IPG connector in the manner well known in the art.

Figure 9:
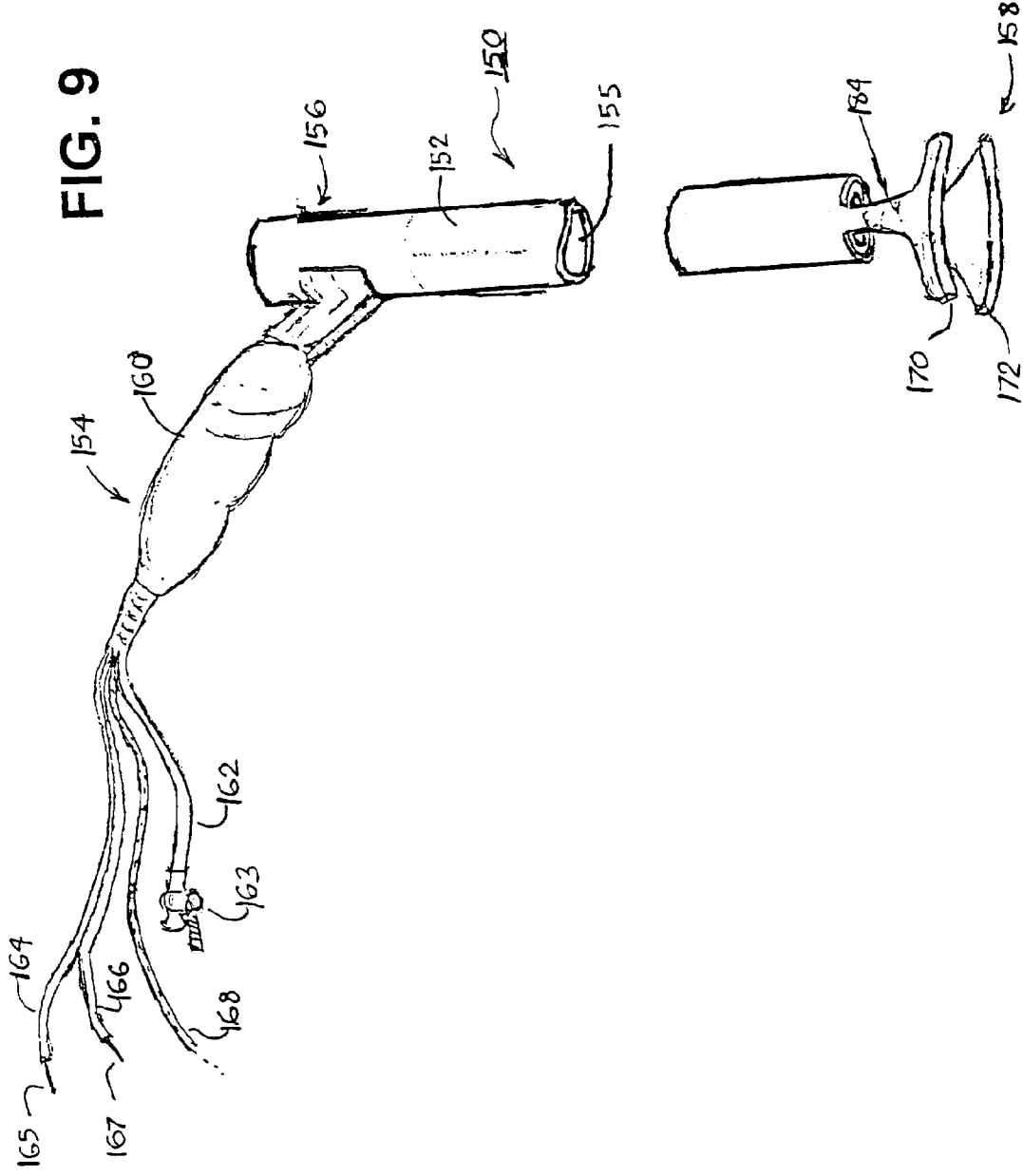
FIG. 9 is a perspective view of a further preferred epicardial lead installation tool of the present invention.

Turning to FIG. 9, a further, simplified, epicardial access tool or lead installation tool 150 is depicted that enables fixation of the epicardium and provides an access lumen 155 through which various instruments can be introduced. The epicardial lead installation tool 150 comprises an elongated tool body 152 and a tool handle 154 extending laterally from the tool body proximal end 156. The tool handle 154 is shaped to provide a handgrip 160 that can be grasped by the user to position the tool body distal end 158 at the desired site of the epicardium. The elongated tool body 152 is generally cylindrical, although it could be made oval to facilitate insertion between the ribs of a patient, and the tool body lumen 155 extends between lumen end openings at the tool body proximal and distal ends 156 and 158.

Again, the suction pads 170 and 172 are preferably formed in an arcuate shape, and the distal surfaces of the suction pads 170 and 172 are preferably concave to optimize gripping of the epicardium. Suction ports, e.g., suction ports 80 and 82 illustrated in FIG. 3, are preferably evenly spaced apart along the concave distal surfaces of the suction pads 170 and 172. The suction pad struts 184 and 186 supporting the suction pads 170 and 172, respectively, are preferably flexible and capable of bending outward when they are loaded by applied force.

Optionally, the tool handle 154 also encloses a pair of conductors that extend between connector elements 165 and 167 of respective flexible lead bodies 164 and 166 and through the elongated tool body 152 to respective pace/sense threshold measurement electrodes 74 and 76, as illustrated in FIG. 3 and described above, along the distal suction pads 170 and 172. The measurement electrodes 74 and 76 are drawn into intimate contact with the epicardium when suction is applied. The connector elements 165 and 167 are connected with a pacing system analyzer (PSA) or the pacemaker implantable pulse generator (IPG) to measure and assess the pacing energy sufficient to capture the heart and the amplitude of the cardiac signals of interest in a manner well known in the art.

Furthermore, the implantation site is optionally illuminated in any of the above-described ways with light transmitted from an external light source. The light can be transmitted through a light conductor 168 and light emitting windows that can be formed in any of the above-described ways of forming light conductor 68.

Figure 10:
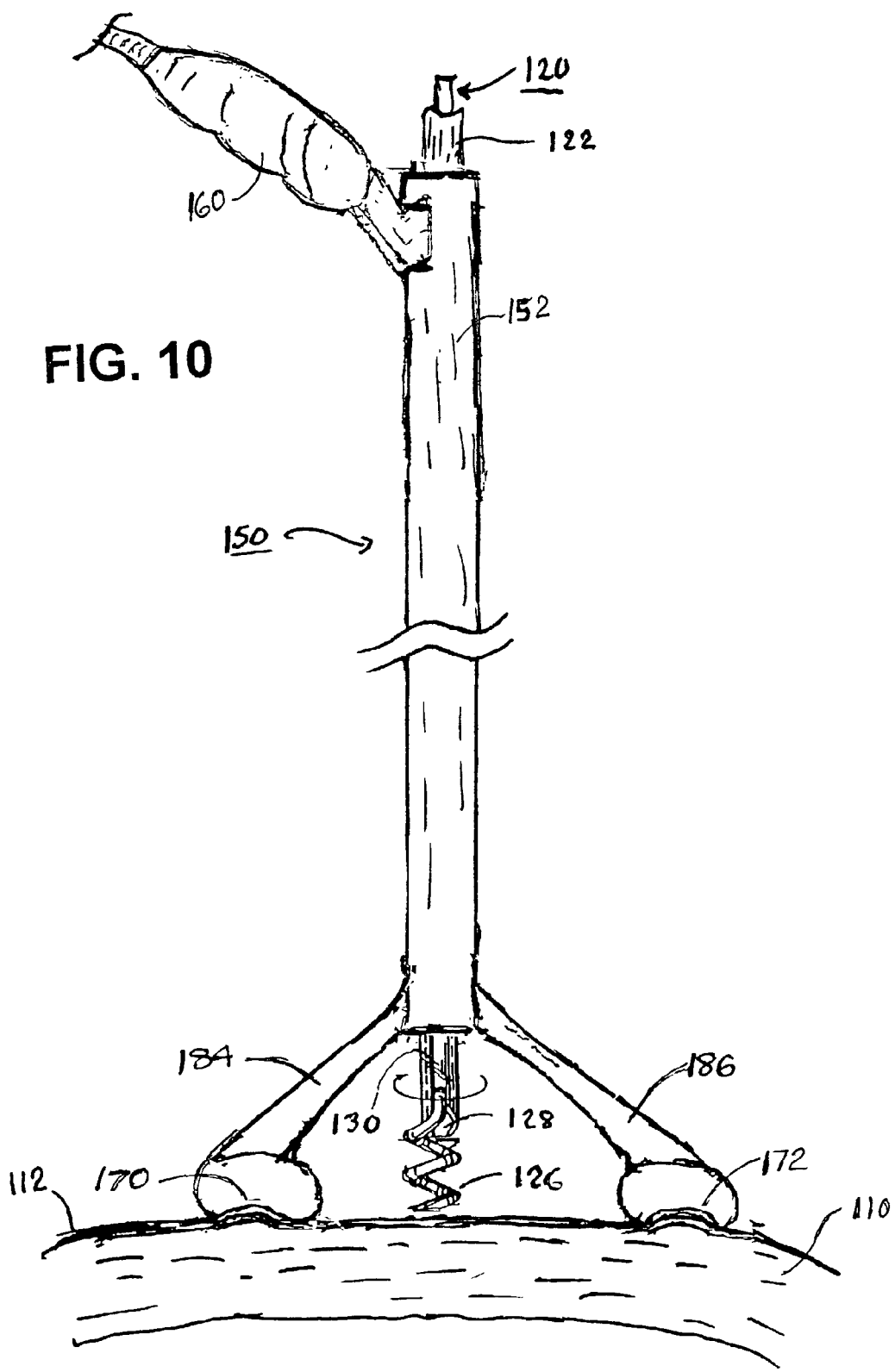
FIG. 10 is a perspective view of a further epicardial screw-in lead assembled with the installation tool of FIG. 9 poised to enable rotation of the helical electrode into the epicardium.

A step in the process of implanting a miniaturized epicardial screw-in pacing lead 120 is depicted in FIG. 10. The epicardial screw-in pacing lead 120 can take any configuration, but the depicted configuration is a highly flexible, small diameter, straight or coiled wire conductor, screw-in lead of the type depicted in commonly assigned U.S. Pat. No. 5,246,014. Such small diameter lead bodies lack "pushability", that is the ability to advance the lead distal end axially when the lead proximal end is pushed axially. The lead bodies of such small diameter screw-in leads are so supple and flexible that it is difficult to rotate the lead distal end by application of rotary torque to the lead proximal end unless the lead body remains relatively straight and not confined by contact with vessel walls. This diminished "torqueability" prevents the rotation of the fixation helix at the lead distal end or renders the rotation unreliable.

The lead 120 is therefore assembled into an introducer 122 that fits over the lead body and engages the electrode head proximal to the distal fixation helix. The inner diameter of the tool body lumen 155 is sufficiently large to receive the outer diameter of the introducer 122 when the assembly is inserted through it. The lead 120 terminates in a distal, electrically uninsulated, helical, screw-in electrode 126 electrically connected to the conductor of lead 120. As further illustrated in FIG. 10, the distal end 128 of the introducer 122 is shaped to engage the shank 130 of the helical screw-in electrode 126 so that it can be rotated by rotation of the proximal end of introducer 122 to screw the helical screw-in electrode 126 through the epicardium 112 and into the myocardium 110. It will be understood that the introducer distal end 128 and the distal electrode head can be configured in other ways so that the electrode head can be rotated and advanced or retracted as the introducer 122 is rotated and advanced or retracted.

It should also be understood that the introducer 122 the tool body lumen 155 can also be formed having mating screw jack threads in the same manner as the outer shaft tubing 26. The introducer 122 is thereby trapped within the tool body lumen 55 for rotation and axial translation to retract the screw-in electrode 126 proximally or extend the screw-in electrode 126 proximally to screw it into the myocardium. In this variation, the thumb wheel 90 can also be provided at the proximal end of introducer 122 to facilitate its rotation and axial advancement or retraction. A mechanism that can be actuated to grip the lead body can also be provided at the proximal end of the introducer 122 to tension the lead body and hold the introducer distal end 128 in engagement with the electrode head.

In use, the lead implantation system is assembled by sliding the lead body proximally through the introducer lumen until the distal end 128 of the introducer 122 firmly engages the shank 130 of the screw-in electrode 126. A mechanism for releasably gripping the lead body can also be provided at the proximal end of the introducer 122 that can be locked so that the distal end 128 of the introducer 122 remains firmly engaged with the shank 130 and released after the fixation helix 126 is screwed into the myocardium 110.

The introducer 122 is retracted to retract the fixation helix proximally, and the epicardial lead installation tool 150 is advanced through the skin incision and positioned as described above with respect to FIG. 6 so that the suction pads 170 and 172 press against the epicardium 112. Suction is then applied so that the suction applied through the suction ports of the suction pads 170 and 172 engages the epicardium 112. Again, the lead installation tool 150 is thereby coupled to and tracks the movement of the heart and the applied suction can stabilize the implantation site to some extent. The implantation site is optionally illuminated, and pacing and sensing threshold tests are optionally conducted as described herein. Rotational torque is imparted to the proximal end of the introducer 122 to distally advance and screw the helical screw-in electrode 126 through the epicardium 112 and into the myocardium 110. Then, suction is released, and the introducer 122 and tool body 152 are retracted through the skin incision leaving the helical screw-in electrode 126 in place.

Pacing and sensing threshold tests are conducted in the conventional manner to determine that the implantation site is suitable. If the thresholds are acceptable, suction is discontinued and the epicardial lead installation tool 150 is removed. The lead body and proximal connector of the lead 120 can then be routed subcutaneously in a conventional manner to the site of implantation of the pacing IPG and attached thereto.

The epicardial lead installation tools 50, 150 can preferably be employed in minimally invasive surgeries through the thorax from a skin incision to implant a plurality of epicardial pacing leads of the type described at selected sites of the left heart chambers, facilitating left heart chamber pacing alone or in conjunction with right heart chamber pacing. The pacing IPG can also incorporate upper and lower heart chamber pacing capabilities as well as cardioversion/defibrillation capabilities.

The stimulation (pacing) and sensing thresholds can be conducted in several ways employing the threshold measurement electrodes 74 and 76 alone or in combination with the epicardial lead 100 or 120. The implantation site can be changed if either threshold is unacceptable. After testing at a suitable implantation site, the sensing and pacing parameters of the IPG can then be adjusted to reflect the determined sensing and pacing thresholds in a manner well known in the art.

To determine the sensing threshold, the proximal connectors 65 and 67 are coupled to a conventional threshold measurement device that can be operated to sense and measure the amplitude of the cardiac signal of interest, typically the R-wave when the implantation site is the left ventricle. The sensing can be conducted in a unipolar or a bipolar configuration of the threshold measurement electrodes 74 and 76. It can be inferred from the sensed signal amplitude that the sensing thresholds will be adequate or inadequate for the IPG that will be coupled to the epicardial lead 100 or 120.

The unipolar pacing threshold can be determined by applying a series of unipolar stimulation pulses at differing pulse energies to one of the threshold measurement electrodes 74 and 76 and sensing the response to the applied pulse at the other of the threshold measurement electrodes 74 and 76. The minimum pulse energy that evokes a cardiac depolarization, i.e., that captures the heart is determined. It is further determined whether the stimulation or pacing threshold is low enough to provide a desired longevity of the battery of the IPG that is to be attached to the epicardial lead 100 or 120.

In addition, adequacy of the unipolar and bipolar (in case the epicardial lead is a bipolar epicardial lead) pacing thresholds can be re-checked by applying the series of pacing pulses through the unipolar pace/sense electrode (or bipolar pace/sense electrodes) of the lead 100 or 120 while sensing for the evoked response at one or both of the threshold measurement electrodes 74 and 76. Difficulties that can arise in sensing the evoked response employing the sensing circuitry of the IPG are avoided in this approach.

The introducer 122 can be removed, and the epicardial lead installation tool 150 can also be used as an epicardial access tool in the manner of a trocar sheath, for example, to introduce other instruments to the epicardium of the heart through a minimally invasive surgical access and/or to perform other procedures on or within the heart. For example, the procedures include introducing and locating the distal end of a catheter or guidewire or an electrode of a cardiac ablation catheter or a cardioversion/defibrillation lead against or through a portion of the epicardium accessed through the tool body lumen. Other possible procedures include performing a coronary artery anastomosis in a thoracoscopic CABG procedure, replacing a defective heart valve, ablating aberrant electrical pathways in the atria to alleviate atrial tachyarrhythmias, introducing drugs or antibacterial agents into the pericardial space, and relieving pericardial fluid pressure. In this variation of the epicardial lead installation tool 150 depicted in FIG. 9, the tool body 152 can be formed of bendable materials so that the user can form a desired bend in it to facilitate reaching a desired fixation location in the myocardium 110.

CONCLUSION

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of implanting an epicardial lead into the myocardium at an epicardial implantation site accessed through the thorax from a skin incision, the epicardial lead of the type having an elongated lead body extending between at least one proximal electrical connector element and a distal fixation mechanism extending from a distal electrode head, the lead body supporting at least one distal pace/sense electrode coupled through an electrical conductor to a proximal electrical connector element, the method comprising:

affixing the distal electrode head to a distal end of a lead implantation tool of an epicardial lead installation tool, the epicardial lead installation tool having an elongated tool body having an inner surface and an outer surface, the inner surface of the tool body enclosing a tool body lumen extending between a tool body proximal end and a tool body distal end, the lead implantation tool extending through the installation tool body lumen such that the distal end of the implantation tool extends out from a distal end opening of the lumen to be disposed adjacent to a suction pad strut of the installation tool, the strut extending distally from the installation tool body distal end to a suction pad supported by the strut, the suction pad having at least one suction port;

grasping a handle of the installation tool to insert the electrode head, affixed to the lead implantation tool, through the skin incision, and to apply the suction pad against the epicardium;

applying suction through the suction port of the suction pad to fix the installation tool body to the epicardium; and rotating a thumbwheel coupled to a proximal end of the implantation tool with a same hand that still grasps the handle, after applying suction, to advance the implantation tool within the lumen of the installation tool body a distance defined by a threaded engagement between an outer surface of the implantation tool and the inner surface of the installation tool body, and, thereby, affixing manipulating the lead the distal fixation mechanism to the myocardium at the implantation site.

2. The method of claim 1, wherein at least one threshold measurement electrode is disposed upon the suction pad and an electrical connector extends from the threshold measurement electrode to a proximal electrical connector adapted to be coupled to a threshold measurement device external to the patient's body and further comprising:

measuring at least one of the stimulation and sensing thresholds of the heart through the threshold measurement electrode applied to the epicardium in the step of applying suction.

3. The method of claim 2, wherein the tool body incorporates a light conductor adapted to be coupled to a light source external to the patient's body and having at least one light-emitting window and further comprising:

emitting light transmitted through the light conductor from the light source through the light-emitting window to illuminate the implantation site.

4. The method of claim 1, wherein the tool body incorporates a light conductor adapted to be coupled to a light source external to the patient's body and having at least one light-emitting window and further comprising:

emitting light transmitted through the light conductor from the light source through the light-emitting window to illuminate the implantation site.

5. The method of claim 1, wherein:

the affixing step comprises inserting the distal electrode head between releasable gripping tongs comprising the distal end of the implantation tool.

6. The method of claim 5, further comprising the step of releasing the gripping tongs from the electrode head.

7. The method of claim 1, wherein the affixing step comprises wrapping the elongated lead body around the installation tool body.

8. The method of claim 1, further comprising the step of emitting light from the tool body distal end to illuminate the implantation site.

9. A system for implanting an epicardial lead into the myocardium at an epicardial implantation site accessed through the thorax from a skin incision, the epicardial lead of the type having an elongated lead body extending between at least one proximal electrical connector element and a distal fixation mechanism extending from a distal electrode head, the lead body supporting at least one distal pace/sense electrode coupled through an electrical conductor to a proximal electrical connector element, the system comprising:

an epicardial lead installation tool including:
an elongated tool body having an outer wall, an inner surface of the outer wall enclosing a tool body lumen extending between a tool body proximal end and a tool body distal end,
at least one suction pad strut extending distally from the outer wall in proximity to a distal end opening of the lumen to terminate in a suction pad that extends through an arc about a longitudinal axis of the lumen, the suction pad having a distal facing surface including at least one suction port, and
a suction lumen extending longitudinally within the outer wall of the tool body between the tool body proximal end and the at least one suction port;
a lead implantation tool including a proximal end and a distal end, the implantation tool extending through the installation tool body lumen such that the lead implantation tool distal end extends out the distal end opening of the lumen to be disposed adjacent the at least one suction pad strut, the lead implantation tool distal end adapted to engage the distal electrode head and the lead implantation tool proximal end being manipulable to affix the distal fixation mechanism at the implantation site, wherein mating threads are formed between an outer surface of the lead implantation tool and the inner surface of the installation tool body outer wall to enable controlled rotation and axial translation of the implantation tool with respect to the installation tool body lumen when the implantation tool proximal end is rotated; and
means for applying suction through the suction lumen to fix the suction pad to the epicardium.

10. The system of claim 9, wherein at least one threshold measurement electrode is disposed upon the suction pad and an electrical connector extends from the threshold measurement electrode to a proximal electrical connector adapted to be coupled to a threshold measurement device external to the patient's body for measuring at least one of the stimulation and sensing thresholds of the heart through the threshold measurement electrode applied to the epicardium through suction.

11. The system of claim 9, wherein the tool body incorporates a light conductor adapted to be coupled to a light source external to the patient's body and having at least one light-emitting window for emitting light transmitted through the light conductor from the light source through the light-emitting window to illuminate the implantation site.

12. The system of claim 9, wherein the epicardial lead installation tool further comprises a tool handle extending laterally to the tool body that can be manually grasped to aim the tool body distal end from the skin incision in a direction toward an implantation site of interest.

13. The system of claim 9, wherein the distal fixation mechanism comprises a fixation helix that is adapted to be rotated through rotation of the proximal end of the lead implantation tool in a screw-in direction to screw the distal fixation helix into the myocardium.

14. The system of claim 13, further comprising a thumbwheel mounted to the proximal end of the lead implantation tool to facilitate rotation of the lead implantation tool within the tool body lumen.

15. The system of claim 14, wherein mating threads are formed between an outer surface of the lead implantation tool and the inner surface of the installation tool body outer wall to enable controlled rotation and axial translation of the implantation tool with respect to the installation tool body lumen when the thumbwheel is rotated.

16. The system of claim 9, wherein:
the distal end of the lead implantation tool comprises releasable gripping tongs movable into a first position that engages the electrode head and movable into a second position that releases the electrode head.

17. The system of claim 16, wherein the implantation tool further includes means for simultaneously releasing the gripping tongs from the electrode head and halting the application of suction through the suction lumen.

18. The system of claim 9, further comprising means for emitting light from the tool body distal end to illuminate the implantation site.

19. The system of claim 18, wherein the means for emitting light comprises an external light source coupled to a light conductor and extending from the light source, along the installation tool body, to a window disposed in proximity to the tool body distal end.

20. The system of claim 19, wherein the window extends around the distal end opening of the tool body lumen.

21. The system of claim 19, wherein the window is formed by a transparent portion of the at least one suction pad strut.

22. The system of claim 19, wherein the window is formed by a transparent portion of the suction pad.

23. The system of claim 9, wherein the at least one suction pad strut is flexible to bend away from the longitudinal axis of the tool body lumen when loaded by an applied force.

24. The system of claim 9, wherein the arc through which the suction pad extends is approximately 45 degrees.

25. The system of claim 9, wherein the arc through which the suction pad extends is approximately 270 degrees.

26. The system of claim 9, wherein the arc through which the suction pad extends is approximately 360 degrees.

27. The system of claim 9, wherein the at least one suction pad strut comprises a pair of suction pad struts extending from the outer wall on opposing sides of the distal end opening of the installation tool body lumen.

28. The system of claim 9, wherein the distal facing surface of the suction pad is concave.

29. An epicardial lead implant system comprising:
an elongated implantation tool including a proximal end, a distal end adapted to reversibly engage an electrode head of an epicardial lead, a thumbwheel disposed in proximity to the proximal end, and an outer surface including a threaded portion; and
an elongated installation tool including a proximal end, a distal end, an outer wall extending from the installation tool proximal end to the installation tool distal end, a lumen enclosed by an inner surface of the wall and extending between the installation tool proximal end and the installation tool distal end, a handle disposed in proximity to the installation tool proximal end and extending laterally from the outer wall, a suction pad strut extending distally from the outer wall in proximity to a distal end opening of the lumen to terminate in a suction pad, and a suction lumen extending within the outer wall between the installation tool proximal end and the suction pad;

wherein the implantation tool is adapted to extend within the lumen of the installation tool such that the implantation tool distal end extends out the distal end opening of the lumen, to be disposed adjacent to the suction pad strut, and the thumbwheel is disposed proximal to a proximal end opening of the lumen and adjacent to the handle of the installation tool; and the inner surface of the installation tool outer wall includes a threaded portion to mate with the threaded portion of the outer surface of the implantation tool, when the implantation tool extends within the lumen of the installation tool, such that rotation of the thumbwheel advances the implantation tool within the lumen.

30. The system of claim 29, wherein the suction pad extends through an arc about a longitudinal axis of the lumen.

31. The system of claim 29, wherein the suction pad strut is flexible to bend away from the longitudinal axis of the lumen when loaded by an applied force.

* * * * *

UNITED STATES PATENT AND TRADEMARK OFFICE
CERTIFICATE OF CORRECTION

PATENT NO. : 7,146,225 B2
APPLICATION NO. : 10/283794
DATED : October 30, 2002
INVENTOR(S) : Guenst et al.

It is certified that error appears in the above-identified patent and that said Letters Patent is hereby corrected as shown below:

On the Title Page of the patent in (74) Attorneys please change "Girma Wold-Michael" to --Girma Wolde-Michael--.

In column 14, line 27, please change "affixing manipulating the lead the" to --affixing the--.

Signed and Sealed this

Ninth Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,146,225 B2 Page 1 of 1
APPLICATION NO. : 10/283794
DATED : December 5, 2006
INVENTOR(S) : Guenst et al.

It is certified that error appears in the above-identified patent and that said Letters Patent is hereby corrected as shown below:

On the Title Page of the patent in (74) Attorneys please change "Girma Wold-Michael" to --Girma Wolde-Michael--.

In column 14, line 27, please change "affixing manipulating the lead the" to --affixing the--.

This certificate supersedes Certificate of Correction issued October 9, 2007.

Signed and Sealed this

Thirtieth Day of October, 2007

JON W. DUDAS
*Director of the United States Patent and Trademark Office*